US006300142B1

(12) United States Patent
Andrewes et al.

(10) Patent No.: US 6,300,142 B1
(45) Date of Patent: Oct. 9, 2001

(54) DEVICE AND APPARATUS FOR CONDUCTING AN ASSAY

(75) Inventors: David Andrewes, Farnham; John Worthington Attridge, Ripley; David Griffiths, Esher; John Phillip Vessey, East Horsley; John Anthony Odell, London; Felix Fernando, Wokingham; Anthony Stevenson, Chester; Mark Gresswell, Broughton; John Curtis, Balderton; David Alan Percival, Hawarden, all of (GB)

(73) Assignee: Provalis Diagnostics LTD, Deeside (GB)

( * ) Notice: Subject to any disclaimer, the term of this patent is extended or adjusted under 35 U.S.C. 154(b) by 0 days.

(21) Appl. No.: 09/555,472

(22) PCT Filed: Nov. 30, 1998

(86) PCT No.: PCT/GB98/03586

§ 371 Date: May 26, 2000

§ 102(e) Date: May 26, 2000

(87) PCT Pub. No.: WO99/28038

PCT Pub. Date: Jun. 10, 1999

(30) Foreign Application Priority Data

| | | |
|---|---|---|
| Nov. 28, 1997 | (GB) | 9725348 |
| Jun. 22, 1998 | (GB) | 9813292 |

(51) Int. Cl.[7] .............................. B01D 63/00; G02B 6/00; G01N 21/84; G01N 33/53; G01N 21/00; B01L 11/00; B01F 11/00; E12M 1/34

(52) U.S. Cl. ............... 436/518; 210/321.61; 210/321.62; 210/321.63; 210/321.64; 210/321.65; 210/321.66; 210/321.67; 210/650; 210/651; 210/782; 385/12; 385/15; 385/33; 385/129; 356/426; 356/427; 422/44; 422/63; 422/64; 422/68.1; 422/82.05; 422/82.11; 422/101; 422/102; 366/208; 435/7.1; 435/7.92; 435/287.1; 435/287.3; 435/287.6; 435/287.7; 435/288.3; 435/288.4; 435/288.5; 435/288.7; 435/297.1; 435/962; 435/967; 436/43; 436/45; 436/63; 436/66; 436/67; 436/88; 436/164; 436/172; 436/174; 436/177; 436/536; 436/538; 436/539; 436/805; 436/807; 436/808; 436/809

(58) Field of Search ............................ 210/321.6, 321.61, 210/321.62, 321.63, 321.64, 321.65, 321.66, 321.67, 650, 651, 782; 356/426, 427; 366/208; 385/12, 15, 33, 129; 414/754; 422/44, 63, 64, 68.1, 82.05, 82.11, 101, 102; 424/530; 435/717.92, 293.1, 962, 967, 287.1, 6, 3, 7, 288.3–288.7; 436/43, 45, 63, 66, 67, 88, 164, 172, 174, 177, 518, 536, 538, 539, 805, 807, 808, 809; 530/363, 380, 412, 417

(56) References Cited

U.S. PATENT DOCUMENTS 3,834,372 9/1974 Turney .................................. 128/2 F (List continued on next page.)

FOREIGN PATENT DOCUMENTS 0 198 413 A 10/1986 (EP) .

(List continued on next page.)

OTHER PUBLICATIONS

International Search Report for PCT/GB98/03586, mailed Mar. 19, 1999.

(List continued on next page.)

*Primary Examiner*—Christopher L. Chin
*Assistant Examiner*—Kartic Padmanabhan
(74) *Attorney, Agent, or Firm*—Hogan & Hartson LLP

(57) ABSTRACT

A apparatus for assaying glycated proteins and other analytes in biological samples such as blood, in which a sample is presented to the apparatus, includes an inlet port between moveable between first and second inlets, such that the inlet can be brought into liquid communication with each inlet in turn. The inlet port accommodates a filter or binder. The apparatus also includes a microprocessor operable via a key pad, at least one light emitter and at least one light detector, a display and driver, and an A to D converter, and is operatively connected to a power source.

20 Claims, 9 Drawing Sheets

U.S. PATENT DOCUMENTS

| | | | | |
|---|---|---|---|---|
| 4,507,977 | * | 4/1985 | Cabrera | 73/864.12 |
| 4,515,889 | * | 5/1985 | Klose et al. | 435/4 |
| 4,676,952 | * | 6/1987 | Edelmann et al. | 422/72 |
| 4,690,801 | | 9/1987 | Anderson | 422/68 |
| 4,695,430 | * | 9/1987 | Coville et al. | 422/65 |
| 4,726,932 | * | 2/1988 | Feier et al. | 422/103 |
| 4,871,683 | * | 10/1989 | Harris et al. | 436/531 |
| 4,889,692 | * | 12/1989 | Holtzmann | 422/102 |
| 4,933,147 | * | 6/1990 | Hollar et al. | 422/64 |
| 4,940,527 | * | 7/1990 | Kazlauskas et al. | 204/401 |
| 4,981,801 | * | 1/1991 | Suzuki et al. | 435/290 |
| 5,008,081 | * | 4/1991 | Blau et al. | 422/64 |
| 5,160,702 | * | 11/1992 | Kopf-Still et al. | 422/72 |
| 5,186,844 | * | 2/1993 | Burd et al. | 210/782 |
| 5,242,803 | * | 9/1993 | Burtis et al. | 435/7.92 |
| 5,270,212 | * | 12/1993 | Horiuchi et al. | 436/45 |
| 5,402,240 | | 3/1995 | Thistlewaite | 356/433 |
| 5,478,750 | * | 12/1995 | Bernstein et al. | 436/164 |
| 5,482,626 | * | 1/1996 | Lohnes et al. | 210/340 |
| 5,496,520 | * | 3/1996 | Kelton et al. | 422/64 |
| 5,507,410 | * | 4/1996 | Clark et al. | 221/171 |
| 5,580,524 | * | 12/1996 | Forrest et al. | 422/63 |
| 5,585,068 | * | 12/1996 | Panetz et al. | 422/64 |
| 5,591,643 | * | 1/1997 | Schembri | 436/45 |
| 5,627,041 | * | 5/1997 | Shartle | 435/7.24 |
| 5,630,986 | * | 5/1997 | Charlton et al. | 422/64 |
| 5,660,727 | * | 8/1997 | Gleave et al. | 210/141 |
| 5,863,506 | * | 1/1999 | Farren | 422/102 |
| 5,885,529 | * | 3/1999 | Babson et al. | 422/65 |
| 6,096,276 | * | 8/2000 | Laursen | 422/103 |

FOREIGN PATENT DOCUMENTS

| | | |
|---|---|---|
| 0 353 025 | 1/1990 | (EP) . |
| WO 91 12515 | 8/1991 | (WO) . |
| WO 96 31619 | 10/1996 | (WO) . |
| WO 97 18036 | 5/1997 | (WO) . |

OTHER PUBLICATIONS

International Preliminary Examination Report for PCT/GB98/03586, mailed Feb. 21, 2000.

* cited by examiner

DEVICE AND APPARATUS FOR CONDUCTING AN ASSAY

RELATED APPLICATIONS

The present invention is a Section 371 filing of PCT/GB98/03586, filed Nov. 30, 1998, which claims priority of GB 97253.48.8 filed Nov. 28, 1997 and GB 9813292.1 filed Jun. 22, 1998.

FIELD OF THE INVENTION

The present invention relates to an apparatus, instrument and device for conducting an assay. More particularly, it relates to a device suitable for use in assaying analytes, for example glycated proteins in biological samples such as, for example, blood.

BACKGROUND OF THE INVENTION

The percentage of total haemoglobin (Hb) that is glycated is widely regarded as an important tool in diabetes management, because it provides an indirect measure of the mean blood glucose concentration over the previous 2–3 months. One of the three main methods available for assaying glycated Hb relies on boronate affinity. In this method glycohaemoglobin can be separated from non-glycohaemoglobin through condensation of solid-phase dihydroxyboronate with the cis-diols present on the sugar moieties of glycohaemoglobin. This method is specific for all glycohaemoglobins which is an advantage over other methods, which rely on separation based on differences in net charge.

However, although the boronate method has certain advantages, it remains an assay which requires laboratory facilities and quite complicated equipment. In particular, the need to determine the percentage of glycated Hb present means that two assay results need to obtained and a comparison made. It is the case that rapid diagnostic assays have been developed, and continue to be developed, which make use of "simple" easy to use diagnostic devices, which can be used either by a subject in their own home, or by a subject's own doctor in the surgery. One example of such a test device is that marketed by Cortecs Diagnostics as HELISAL®ONE-STEP, which is for the detection of H. pylori infection. The principle of this device is, however, generally applicable to a range of assays. The device consists of two parts, a sample collector and a second part containing an assay strip. The collector is used to collect a sample (of blood in the case of HELISAL®ONE-STEP) and the collector is then inserted into the second part, with which is interconnects, to release the sample to an assay strip. The sample travels along the strip through various "zones" which contain various reagents, including a coloured label (blue latex particles). If antibodies to H. pylori are present then the label concentrates in a detection zone. The specifics of this particular assay are not important, however. The essential features which are common to this type of assay and which allow its use in their home or doctor's surgery are the ease of sample collection and handling as well as the simplicity in initiating the reaction and the speed with which the result is obtained. Such one-step devices can be utilised in the measurement of glycated Hb but only if the assay method can incorporate the necessary sample treatment to allow comparison of total protein with glycated protein.

SUMMARY OF THE INVENTION

To that end, therefore, we have in a first aspect of the invention devised an apparatus which allows rapid, easy sample treatment combined with compatibility with a one-step device such as that exemplified by HELISAL®ONE-STEP.

According to a first aspect the present invention there is provided an apparatus, for use in an assay in which a sample is presented to an instrument, comprising a first inlet, a second inlet, and an inlet port, said inlet port being moveable relative to each of said first and second inlets such that the port can be brought into liquid communication with each inlet in turn as required, wherein said inlet port accommodates a filter means or a binder retaining means.

In one embodiment the apparatus is adapted to be used in an assay system where some form of particulate is added to a sample which may contain a detectable analyte, where the particulate is capable of binding the analyte. Thus when the sample plus particulate is added to the inlet port, the particulate, with bound analyte, is retained by the filter. The filter can of course be constructed of any suitable material. Suitably, it will be made of material which is inert in terms of the analyte etc. Also the "mesh" of the filter must be such that it is capable of retaining particulates as used in the separation step. The inlet port can then be moved into alignment with the second inlet means and one or more reagents capable of interfering with the binding of the analyte to the particulate can be added to the inlet port. The analyte (if present) will then pass through the filter in solution, leaving the particulates behind.

Thus, taking the example of glycated Hb, a sample of blood is treated to lyse the blood cells and is then admixed with particulates, eg agarose or cellulose, to which is bound phenyl boronate. The treated sample is then introduced into the apparatus via the inlet port, which will have been moved into liquid communication with the first inlet. The liquid part of the sample, which contains non-glycated Hb, will pass through into the body of the apparatus, while the particulates, to which will be bound any glycated Hb, will be retained by the filter means associated with the inlet port. The inlet port can then be moved into liquid communication with the second inlet and the particulates can be washed with one or more suitable reagents to cause release of the bound glycated Hb from the particulates.

In an alternative approach, the inlet port can incorporate means capable of binding the analyte. For example, it could incorporate particulates such as those described above. Thus, in one embodiment the invention provides apparatus for use in a diagnostic assay, comprising a first inlet, a second inlet and an inlet port, said inlet port being moveable relative to each of said first and second inlets such that the port can be brought into liquid communication with each inlet in turn as required, wherein said inlet port incorporates binding means, capable of binding an analyte which may be present in a biological sample. Such an apparatus would of course also incorporate some means of retaining the binding means in the inlet port.

In preferred embodiments of both the above-described aspects of the invention, the apparatus will also incorporate a third inlet, and the inlet port will be capable of being moved between the three inlets as required. The third inlet will ideally be placed in an intermediate position between the first and second inlets. The provision of this third inlet will allow for an intermediate washing step to be carried out prior to treating the binding means to release the analyte. In one embodiment the apparatus will be generally circular and the inlet port will form part of a rotatable top portion of the apparatus.

In another embodiment the inlet port will be stationary and the first and second inlets will rotate into communication with the inlet port As described above the apparatus of the present invention allows a relatively unskilled operative to treat samples, eg blood samples, for assaying in systems such as that used for measuring glycated haemoglobin.

In a preferred embodiment of the above described aspects of the invention the apparatus is designed to be used in conjunction with one-step assay devices such as those described in WO 97/18036. Thus, the apparatus of the present invention can be adapted to allow insertion of one or more sample collectors as described in WO 97/18036. In practice the one or more sample collectors will be inserted such that they are in liquid communication with the first and/or second inlets. Thus, in use, a first sample collector can be inserted such that it is in liquid communication with the first inlet. In the case of the first aspect described above, the inlet port will also initially be in liquid communication with the first inlet and the sample plus particulate is added to the inlet port which will retain the particulate, and any bound analyte, allowing the rest of the sample to pass through for collection by the first sample collector.

This sample collector can then be removed and inserted into a test instrument as described in WO 97/18036. The inlet port can then be moved to the intermediate inlet (if present) and wash buffer can be added, flowing through and into a sink incorporated in the apparatus. The inlet port can them be moved into liquid communication with the second inlet and one or more reagents can be added to dissociate the analyte from the particulates. A second sample collector can then collect the analyte solution for removal and insertion into a second one-step device.

Thus, in the case of assays for glycated haemoglobin, the two results obtained can be used to calculate a percentage value for glycated haemoglobin. Conveniently, this can be done using a device such as Cortecs' INSTAQUANT reader which has been designed for use with one-step assay devices.

Suitably, the apparatus of the invention will be constructed of a liquid impervious material such as plastic.

In a more preferred embodiment, the apparatus of the invention is adapted such that the respective samples passing through the first and second inlets are collected in optical chambers disposed below said first and second inlets or said first and second inlets and/or include optical chambers. Thus, in one embodiment the invention provides an apparatus for use in a diagnostic assay comprising a first inlet, a second inlet and an inlet port, said inlet port being movable relative to each of said first and second inlets such that the port can be brought into liquid communication with each inlet in turn as required, wherein said first and second inlets are in liquid communication with associated optical chambers.

The apparatus is connectable to an instrument which incorporates means for the spectrophotometric measurement of said samples in the optical chambers.

According to a second aspect of the invention there is provided an instrument, for reading a sample presented in an apparatus, comprising a microprocessor operable via a key pad, one or more light emitters and one or more light detectors, a display and driver, an analogue to digital converter, and means for connecting the instrument to a power source.

Preferably each optical chamber houses a micro-cuvette and the instrument comprises means for measuring the absorbance of the contents of each micro-cuvette. Thus, the instrument comprises a LED light source to generate electromagnetic radiation at one side of the sample and an associated photodiode (PD) for measuring the intensity of transmitted light generated across the sample i.e. the instrument measured absorbency. Preferably, the instrument comprises one or more LED/PD pairs. In one embodiment one or more LED/PD pairs are arranged such that when the instrument is connected to the apparatus one or more LED/PD pairs are disposed across each optical chamber.

In another embodiment the apparatus and instrument are connected such that one or more LED/PD pairs are positioned such that a reading can be taken of a sample in the first optical chamber and then the same one or more LED/PD pairs can be moved to read the sample in the second optical chamber. Alternatively the optical chambers can be moved relative to the one or more LED/PD pairs.

Producing an instrument with means for the spectrophotometric measurement of said samples proved problematic, since it was necessary to overcome two conflicting problems, namely that:

1. In normal sleep mode, the current drain was only in the order of $\mu$ amps and as a consequence was insufficient to prevent a passivation layer from building up within the electric cell/battery used to drive the instrument, so significant voltage drops occurred when the instrument had not been used for some time; and
2. when running a test, the intermediate loading from the LED's and analogue circuitry was not sufficient to dispose the passivation layer.

In order to overcome these problems it was necessary to:

1. select a lithium thionyl chloride battery;
2. condition it,
   (Conditioning can be achieved by for example applying a IK Ω load for 24 hours. The skilled man will, however, appreciate that higher loads for shorter period are effective); and
3. regularly switch in a load for a short period of time.

In one embodiment a 3.6 V lithium thionyl chloride battery is conditioned by applying a 3.3 K Ω load for 7 to 8 hours before soldering the battery onto the main PCB. This assures that the passivation state of the battery is consistent. The processor is controlled to wake every second by switching in a 1 K Ω load for 3.5 mS.

One embodiment of the invention provides an instrument comprising a microprocessor operable via a key pad, one or more light emitting diodes (LED's) and one or more associated photodiodes, a display and driver, an analogue to digital converter, a lithium thionyl chloride battery and a battery conditioning circuit.

The battery is conditioned prior to its incorporation, and soldered, onto a printed circuit board. Conditioning reduces internal resistance in the battery which would result in inconsistent voltages and readings with unacceptable variation.

Circuitry and software is provided to maintain the battery conditioning by repeated discharge of the battery.

Also circuitry and software control systems that energise the LED's in a timed sequence, to permit voltage recovery to stable levels before circuit noise readings are taken and the next reading cycle commenced are provided.

According to a third aspect of the invention there is provided a device comprising an apparatus and an instrument of the invention.

In a particularly favoured embodiment the apparatus of the invention comprises three main components:

a base portion; a top portion and a funnel portion which serves as the inlet port.

The top portion is connected to the base portion to form a carousel and the funnel portion fits within the top portion such that it can in turn communicate with optical chambers present in the base portion.

The funnel portion has a stem which extends from its centre and serves to connect the apparatus to the instrument. The inlet port funnels the sample and reagents in turn into the respective inlets of the base portion and has an outlet displaced from the centre of the funnel. The outlet is designed to either accommodate a filter means or retain a binding means. Preferably a frit sits within the outlet supported by, for example, a narrowing of the outlet or a flange. The funnel portion further comprises an annular ring which serves as a guide member about which the carousel comprising the top portion and base portion rotate. The annular ring has a cut away or recessed portion thereby allowing tubes, housed vertically in the carousel, to be presented to the user at the appropriate times during the assay procedure. Housing the tubes vertically reduces the size of the apparatus and reduces packaging costs. An inclined ramp disposed on the floor of the instrument upon which the apparatus sits cause respective tubes to be lifted through openings in the top portion as the carousel is rotated on the instrument. The annular ring thus also functions to retain the rubes until they are ready for presentation thus making sure the assay reagents are presented in a correct order.

The top surface of the top portion, as noted above, comprises a plurality of apertures through which respective tubes containing the reagents pass.

The top portion also has an indicator means, which denotes the position for location of the apparatus on the instrument. Preferably, this is in the form of a projecting member which assists the operator to turn the apparatus in the instrument, and more particularly it can be aligned with markers denoting operating positions on the instrument.

The base portion comprises a guide member of a guide pair, which in use co-operate with the other members of the guide pair on the instrument. In a preferred embodiment the base portion has on its side a guide member, for example, in the form of a projecting member which enables the apparatus to be retained and moved in an annular channel in the instrument. The guide member also importantly functions to maintain the optical chambers of the apparatus in a position such that accurate readings can be taken. The base portion comprises a first and second inlet in the form of optical chambers which optical chambers can be rotated with the base portion to be in liquid communication with the inlet port. The optical chambers have a geometry so that the LED's in the instrument can be positioned at the centre of curvature. This has the advantage that all rays in the horizontal plane will be perpendicular to the walls of the optical chamber and should not be subjected to refraction. This relaxes rotational location tolerances of the apparatus.

Preferably the optical surfaces of the optical chambers will be recessed to avoid damage on rotation and prevent a risk of them picking up dirt on handling.

The third inlet which need not be an optical chamber will preferably contain a means for drawing the wash liquid through. Such means might include an absorbent or wicking material such as, for example, filter paper. Other materials such as, for example, acetate based weaves, felts and the like could, however, be used.

Preferably the top and base portions are connected in a manner such that used—reagents are sealed therein. This is most conveniently achieved using a ring seal between the portions.

Preferably, the base unit is made of a clear material, although depending on the application of the apparatus a tinted or coloured material, preferably plastics could be used. Alternatively, an optical filter can be positioned in front of the optical chamber and a white light source used. The optical filter is preferably a wavelength filter.

The apparatus is intended to be disposable.

The apparatus is designed to operate on a ratchet mechanism so that it can only be rotated in one direction on the instrument.

In a particularly favoured embodiment the instrument is run, not from a lithium thionyl chloride battery under the control of a battery conditioning circuit but from an external source, for example, a mains source or car battery via a transformer. Consequently, the apparatus is provided with a power management and monitoring circuit. Preferably the instrument is provided with a communication system such as, for example, an RS 232 thereby providing means for sending and receiving instructions and down loading data.

The instrument's electronics are housed in a case which is specifically adapted for use with the apparatus of the invention. It comprises a recess into which the apparatus of the invention sits. The recess is defined by a floor, an innermost side wall (which is the outer wall of a spigot projecting from the floor) and an outermost side wall. The spigot which projects upwards from the floor of the recess has a portion which mates with a recess in the stem of the funnel portion of the apparatus. Thus, the recess is substantially annular. The outermost side wall has a channel member running about its circumference. This channel is shaped to accept a guide member projecting from the apparatus. This arrangement enables smooth rotation of the apparatus in the instrument and importantly assist in aligning the optical chambers of the apparatus with the light emitter/light detector arrangement of the instrument. The light emitter/light detector arrangement preferably comprises a LED/PD arrangement. The LED's and photodiodes are most preferably arranged such that the reading path of the instrument lies across part of the annular recess. Thus, the innermost and outermost side walls are provided with respective windows through which a path of light from the LED's to the photodiodes can travel. Most preferably the LED's are housed in the outermost wall and the light passes through the optical chamber towards the spigot in which the photodiodes are housed. The LED's and photodiodes could, however, be arranged the other way around. However, with the former arrangement the convex face of the optical chambers help focus the light giving more accurate readings.

Another feature of the instrument design is a connecting channel running from the top surface of the instrument to the circumferential channel member so as to allow the guide member of the apparatus to be inserted in a set position. Once the apparatus is rotated it is locked in the instrument until it returns to the connecting channel from which it can exit. Also, a ramp is provided on the floor of the instrument's recess so that when the tubes housed in the apparatus contact the ramp as the apparatus is rotated they are lifted presenting them to the user.

BRIEF DESCRIPTION OF THE DRAWINGS

The various aspects of the invention will now be described by way of example only, with reference to the following figures in which.

DETAILED DESCRIPTION OF THE PREFERRED EMBODIMENTS

Figure 1:
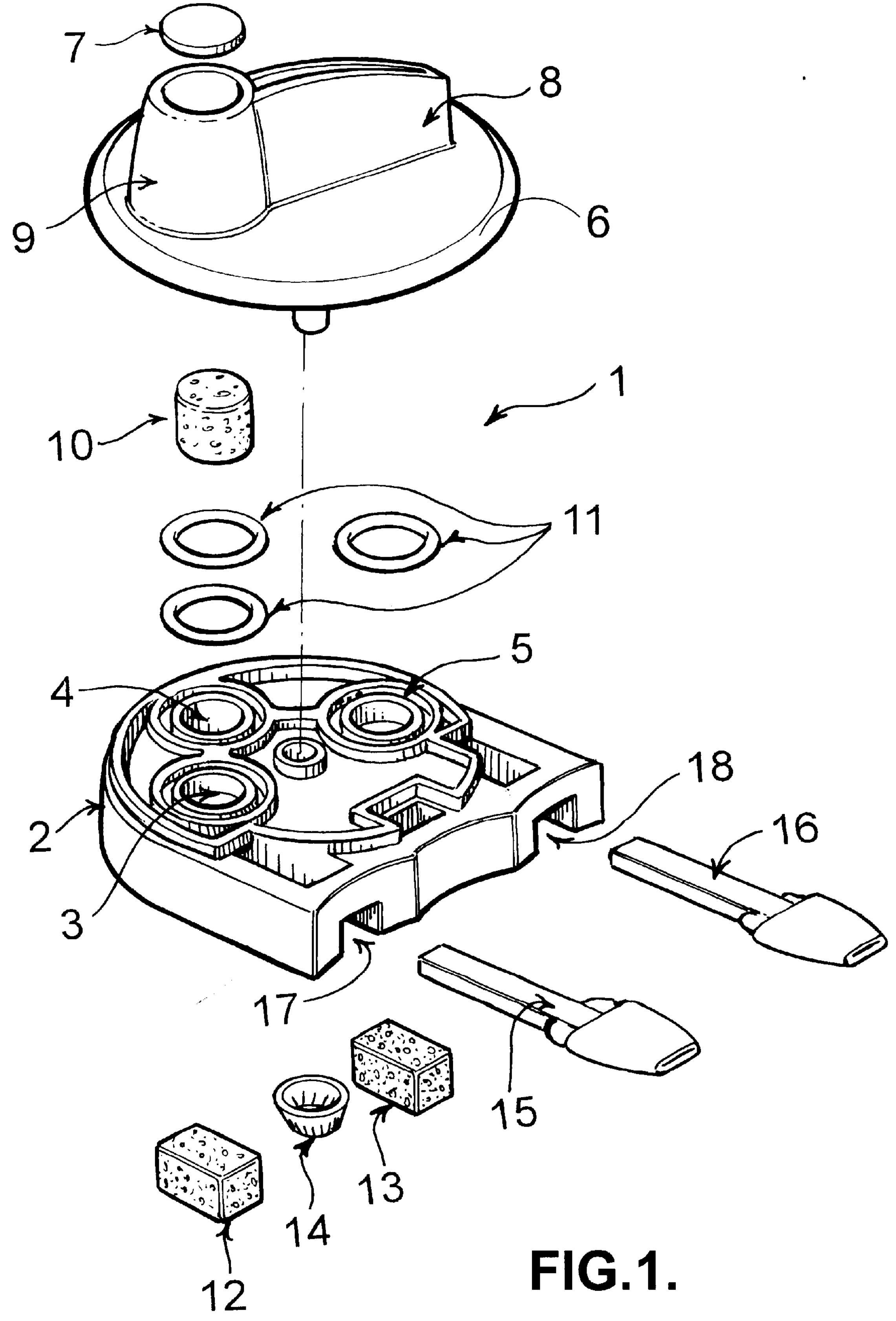
FIG. 1 is a perspective view of an embodiment of the first aspect of the present invention.

Referring to FIG. 1, the apparatus 1 comprises a base section 2 and a rotatable top portion 6. The rotatable top portion 6 itself comprises a handle section 8 and an inlet port 9, the inlet port incorporating a filter means 7. The base section 2 has three inlets 3, 4 and 5 which are associated with three "O" rings 11. A foam pad "sink" 10 is inserted in the middle inlet 4 to collect washing buffer. In this embodiment similar foam pad "sinks" 12 and 13 are associated with the other inlets 5 and 6. The rotatable top portion 6 is retained in place by means of a spring clip 14. Also shown in FIG. 1 are two sample collectors 15 and 16 which can be inserted into the apparatus 1 by way of openings 17 and 18 such that they will be in liquid communication with the inlets 3 and 5.

Thus, in operation, the top portion 6 is first moved to a first position where the inlet port 9 is aligned with the first inlet 3. A first sample collector 15 is inserted in the first opening 17. The sample plus particulate is then added to the inlet port 9, where the particulates will be retained by the filter means 7 allowing the liquid phase to pass through where it is taken up by the sample collector 15. Any excess liquid will be retained by the "sink" 12.

The top portion 6 is then moved to a second position where the inlet port is aligned with the intermediate inlet 4 and wash buffer is added to wash the retained particulates. The wash buffer passes through and is retained by the "sink" 10.

The top portion 6 is then moved to a third position where the inlet port 9 is aligned with the remaining inlet 5. One or more suitable reagents is then added to cause the analyte to dissociate from the particulates and pass through the filter means 7 to be collected by a second sample collector 16 inserted in the apparatus 1 by means of the second opening 18. Each sample collector can be removed and assays carried out in accordance with the principles described in WO 97/18036.

According to a fourth aspect of the present invention there is provided an assay, conducted using an apparatus of the invention wherein a sample is separated into a first component fraction and a second component fraction and the assay determines the presence or absence of one or more analytes in said sample fractions.

As described above, the apparatus of the present invention is particularly suited to use in assays for glycated proteins such as glycated haemoglobin. Thus, in one embodiment the present invention provides an assay for determining the percentage of one or more glycated proteins present in a blood sample, which comprises the step of using an apparatus as described herein to separate a blood sample into a first component comprising one or more non-glycated proteins and a second component comprising one or more glycated proteins.

Preferably, the assay further includes one or more of the following steps:

(i) obtaining a blood sample from a subject;

(ii) treating the blood sample obtained in (i) to lyse the blood cells; and (iii) providing to the sample obtained in (ii) a means for binding glycated proteins, for example a solid phase to which is bound one or more reagents capable of binding glycated proteins.

Examples of glycated proteins which can be assayed using this method include glycated haemoglobin, glycated human serum albumin and glycated apo lipoprotein B. These proteins will be bound by the boronate ligand and so an assay can be performed in which all three glycated proteins will be bound to a particulate. The component containing all three glycated proteins can then be collected and individual assays can be run to determine the relative amounts of each glycated component. Alternatively, a single one-step device could be used which had three individual capture zones bearing a reagent specific for each of the three glycated proteins. The relative amounts could then be determined using a device such as the INSTAQUANT reader.

An apparatus of the present invention can be included in a kit for use in an assay for one or more glycated proteins. Thus, in a further aspect the present invention provides such a kit comprising an apparatus of the invention and optionally one or more sample collectors or one step assay devices or reagents. Examples of suitable one-step assay devices include those described in WO 97/18036, although the skilled person will appreciate that any device designed to allow an assay to be carried by simple addition of a sample to an assay strip can be used.

Another major advantage of the apparatus of the present invention results from the ability to combine a "chemical" or biological capture or separation step, such as the use of the boronate ligand, with an immunoassay or a hand held spectrophotometric means.

According to a fifth aspect of the present invention there is provided a kit comprising an apparatus according to the invention and optionally one or more sample collectors or one step assay devices or reagents and/or a capillary tube and/or an inoculating loop.

According to a sixth aspect of the present invention there is provided a point of care method for the detection of an analyte in sample which comprises:

(i) separation of the analyte from the sample by the use of chemical or biological means; and (ii) detection/quantifying the analyte by means of an immunoassay or spectrophotometric means.

As used herein "chemical" means the use of one or more reagents whose interaction with the analyte is primarily chemical and not biological. For example, as described herein, a boronate based separation step can be used to separate glycated proteins from non-glycated proteins in a sample. Preferably, step (i) is achieved using apparatus according to the present invention and step (ii) is achieved by means of a one-step assay device.

In a preferred embodiment the apparatus of FIG. 1 is modified to include optical chambers thereby allowing the samples collected to be read spectrophotometrically.

Figure 2:
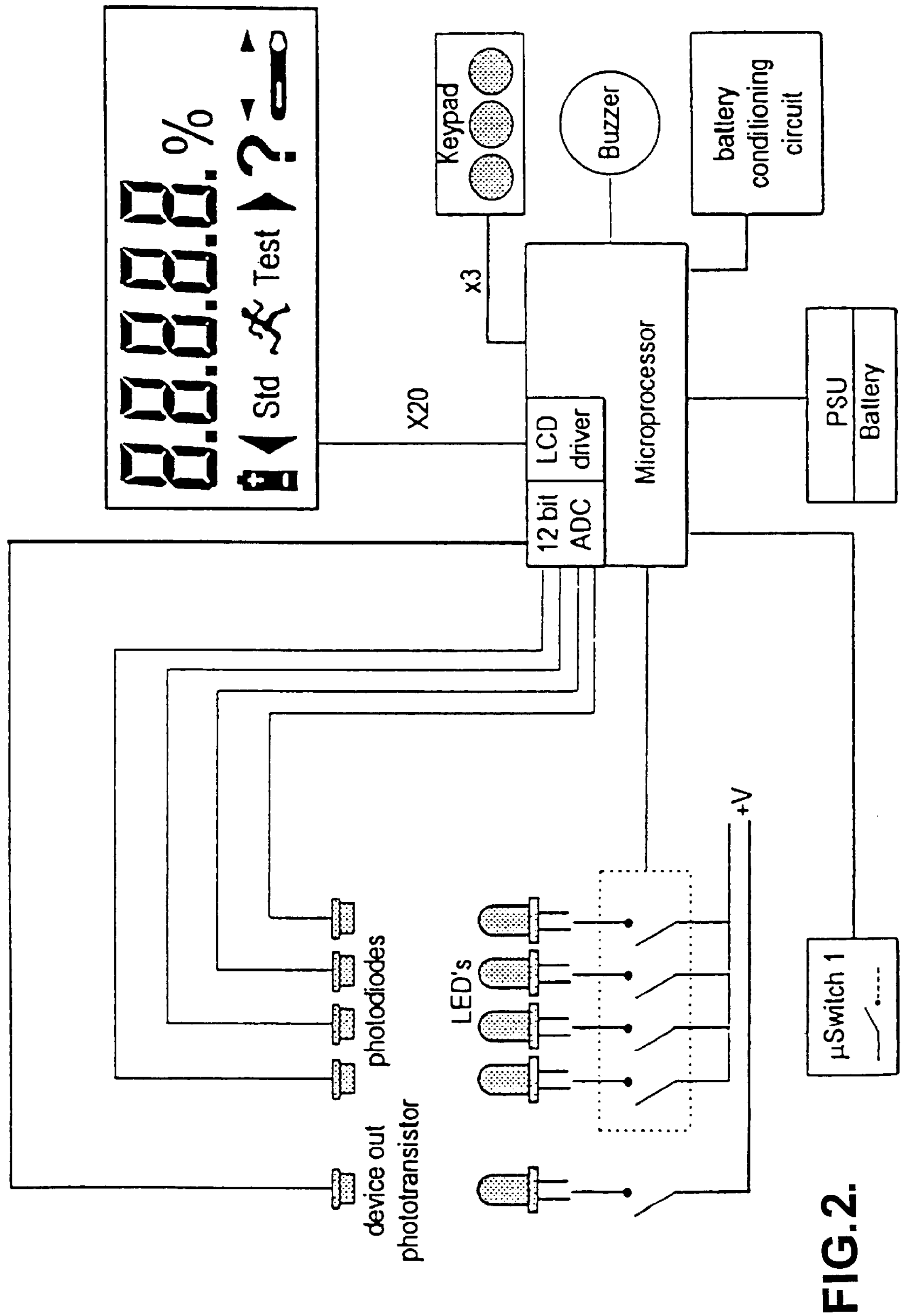
FIG. 2 is a block diagram showing the electronics of an instrument of the 4th aspect of the present invention.

Preferably the discrete optical chambers house micro cuvettes. By measuring the contents absorbance at a given wave length more accurate readings, than can be obtained using reflected light, can be obtained. Thus, preferably the apparatus is adapted to be connected to an instrument with means for measuring the absorbence of the liquid collected in the optical chambers. FIG. 2 is a block diagram illustrating the essential components of one such instrument.

Thus, the instrument comprises a body housing a micro processor powered by a lithium thionyl chloride battery under the control of a battery conditioning circuit. Instructions can be transmitted to the micro processor via a key pad and information/instructions presented via a liquid crystal display powered by a LDC driver. The micro processor controls one or more LED's which pass light of a given wave length (420–430 nm in the case of an instrument for reading glycated haemoglobin) across the optical chambers such that absorbed light is measured by photodiodes. The readings are communicated to the liquid crystal display via an analogue digital converter. A micro switch determines that the device (apparatus and instrument) is activated by the correct connection of the apparatus to the instrument. A LED/phototransistor pair is provided to determine when the apparatus has been disconnected from the instrument.

Figure 3:
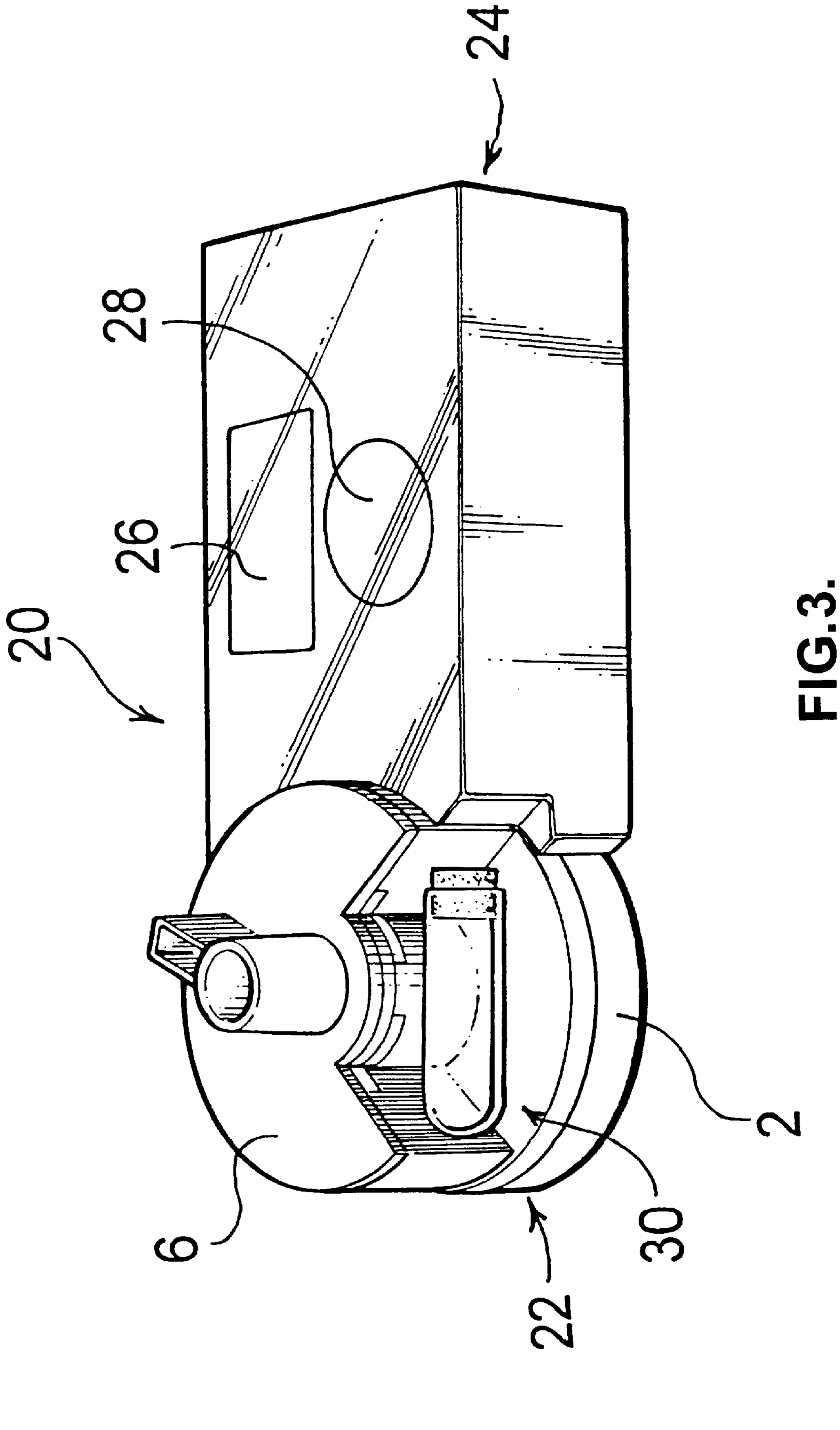
FIG. 3 is an embodiment of a device of the present invention.

Electronics of the type illustrated in FIG. 2 and controlling software are incorporated as an integral part of the instrument. The device resulting from the connection of the apparatus and instrument is illustrated with reference to FIG. 3. Thus, the device 20 comprises an apparatus 22 similar to the apparatus 1 of FIG. 1 and an instrument 24 which houses the electronics.

Apparatus 22 differs from the apparatus of FIG. 1 in that the inlets (which correspond to inlets 3, 4 and 5 of FIG. 1) communicate with optical chambers in the base 2 of the apparatus. The apparatus and instrument are connected to one another via respective mating members such that a or respective LED/photodiode pairs present in the instrument are situated on either side of the optical chambers or can be presented in turn to said respective optical chambers so enabling absorbance readings to be taken and communicated to the display 26 provided in instrument 24. A key pad 28 is also provided in instrument 24. The top 6 and base 2 of apparatus 22 are designed to include a chamber 30 for housing one or more components of a kit, for example reagents such as a wash solution and/or buffer and/or elution buffer and/or a capillary tube. The chamber 30 is shown in its open position in FIG. 3.

Figure 4A:
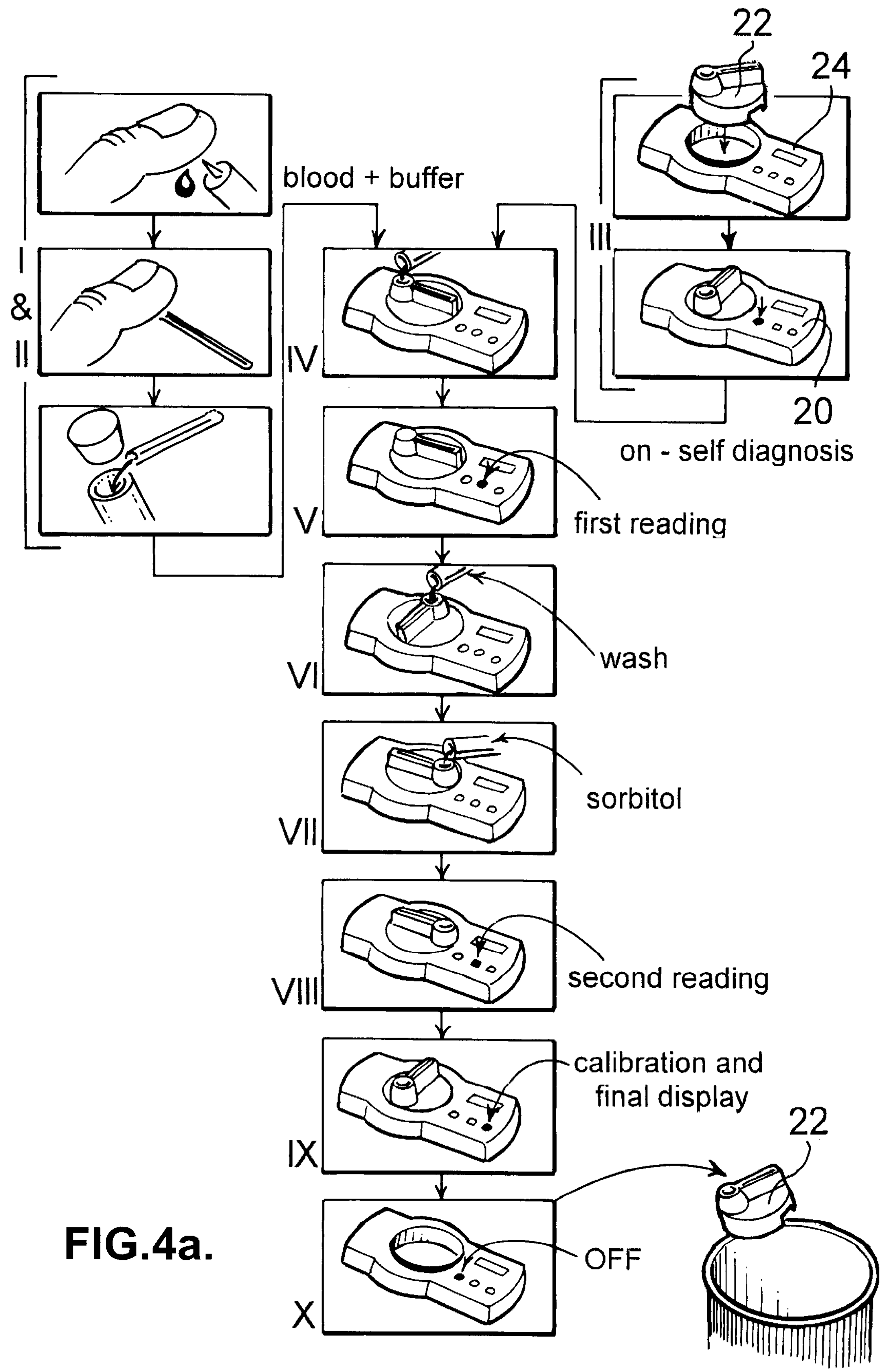
FIG. 4*a* is a schematic showing how the device of FIG. 3 is used in an assay.

Referring to FIG. 4 a protocol for operation of the device is as follows:

(i) A finger-prick blood sample is collected into a capillary tube and placed into the sample buffer tube which contains a buffer and an amino phenyl boronate (aPBA) agarose affinity matrix. The tube is capped and inverted several times, which washes the blood out of the tube and into the buffer where the red blood cells are lysed thus liberating the haemoglobin.

(ii) The tube is left for approximately 60–90 seconds, with occasional inversion, during which the glycated haemoglobin present in the sample binds to the aPBA affinity matrix.

(iii) During this time, the apparatus 22 which is designed to be disposable, is coupled to the instrument 24. The location of the apparatus to the instrument activates the on switch.

(iv) After about 60–90 seconds incubation, the contents of the sample buffer tube are mixed by repeated inversion and then the entire contents are poured into the inlet port which is located in position 1.

(v) The liquid contents of the tube drain through a frit or other filter means located at the bottom of the first inlet and collect in an optical chamber in the base of the apparatus 22. The aPBA affinity matrix, however, is too large to pass through the frit and therefore collects in the column at the bottom of the first inlet.

(vi) The liquid contents collected in the first optical chamber contain the non-glycated haemoglobin present in the original sample, the aPBA affinity matrix collected in the bottom of the inlet port 9 contains the glycated haemoglobin present in the original sample.

(vii) On completion of this first step, the instrument directs the user to progress to stage 2, which is accomplished by turning the top part of the apparatus 22 through 90° and stopping at position 2. Again under the direction from the instrument 24 a specific volume of wash buffer is added to the inlet 2 via inlet port 9 and allowed to drain through. This step is to remove any non-specifically bound non-glycated haemoglobin from the aPBA affinity matrix that may be present from step 1.

(viii) The instrument 24 then directs the user to progress to stage 3 and add the contents of the elution buffer tube to the inlet 3 via inlet port 9 which is allowed to drain through the frit and collects into a second optical chamber in the base of the apparatus 22. The elution buffer removes the glycated haemoglobin from the aPBA affinity matrix.

(ix) The instrument 24 then spectrophotometrically measures the absorbance (at 430 nm) of both the non-glycated and the glycated haemoglobin fractions present in the two optical chambers. Using an algorithm built into the instrument software, the % glycated Haemoglobin present in the original whole blood sample is calculated and displayed on the display 26.

(x) The apparatus 22 is disconnected from the instrument 24 and is discarded as biohazardous waste. The instrument is then ready to perform the next test.

Figure 4B:
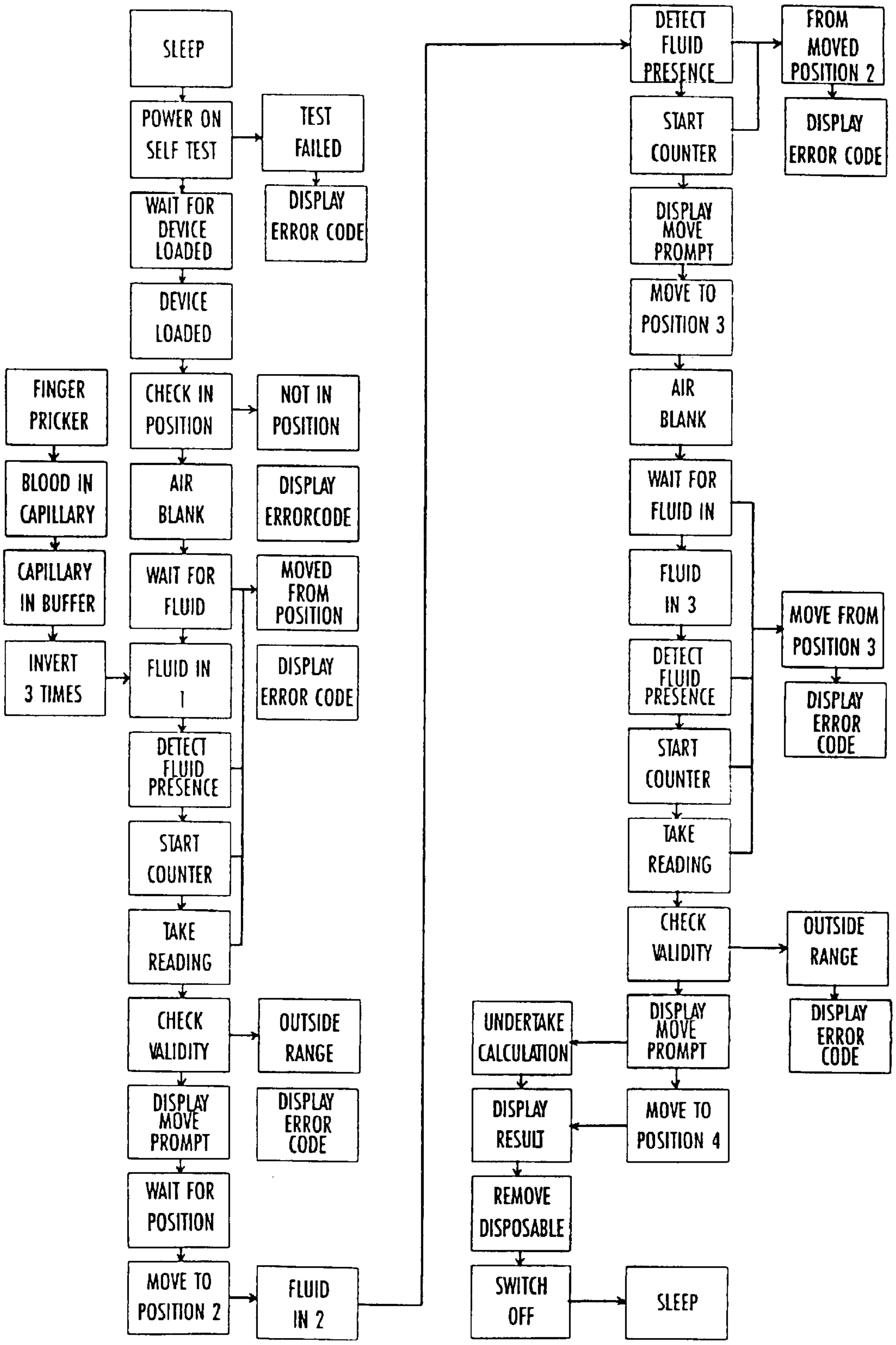
FIG. 4*b* is a flow chart showing a protocol for the use of the device shown in FIG. 3.

More particularly the instrument is controlled to operate in accordance with the protocol outlined with reference to the flow diagram shown in FIG. 4*b*.

The spectrophotometric measurement of both glycated and non glycated haemoglobin fraction occurs at the interface of the optical chambers of the apparatus with the instrument 24 of the device.

Figure 8:
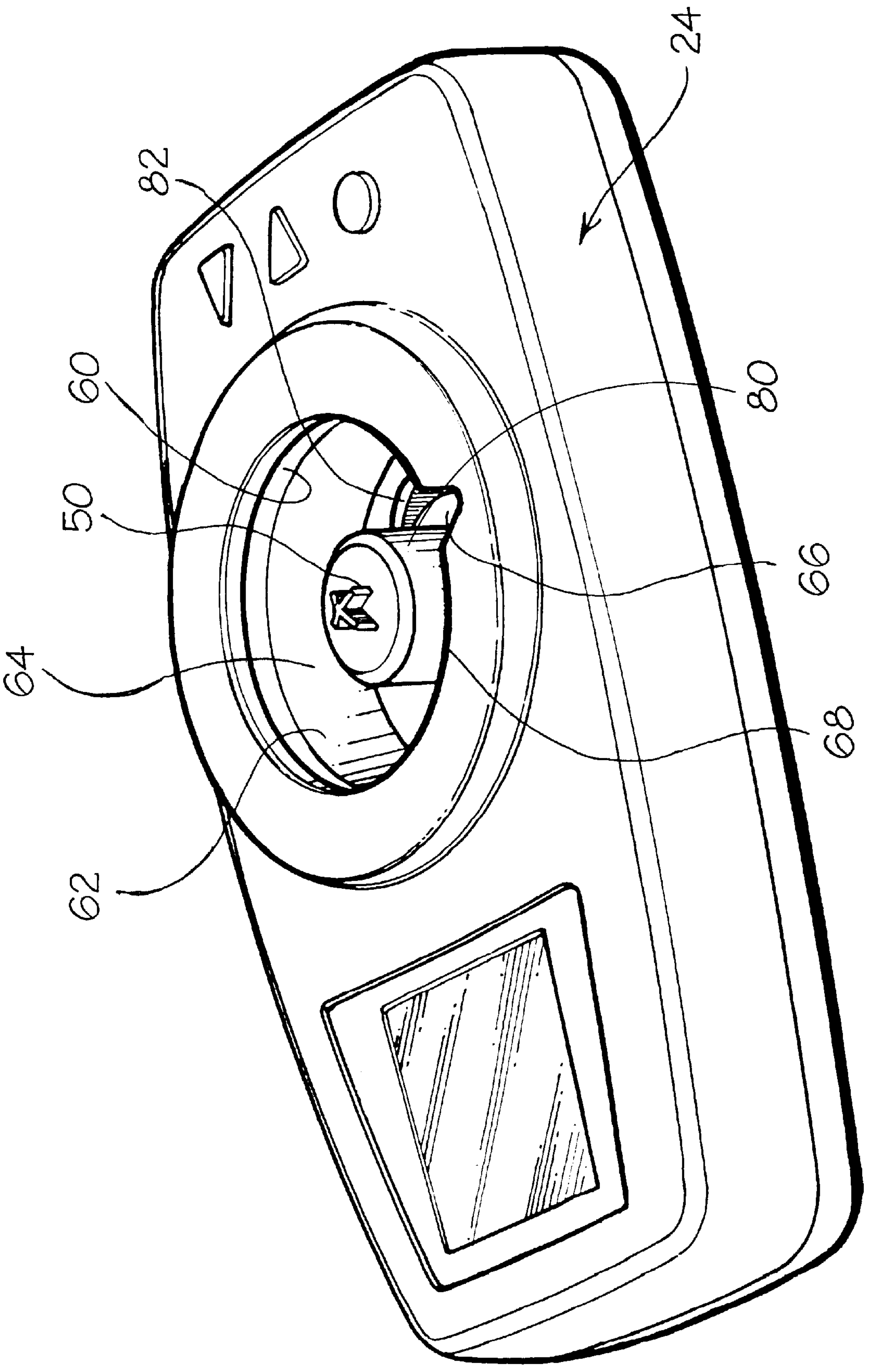
FIG. 8 is a perspective view of a preferred embodiment of an instrument of the invention for use with the apparatus illustrated in FIGS. 5 and 6.
Figure 9:
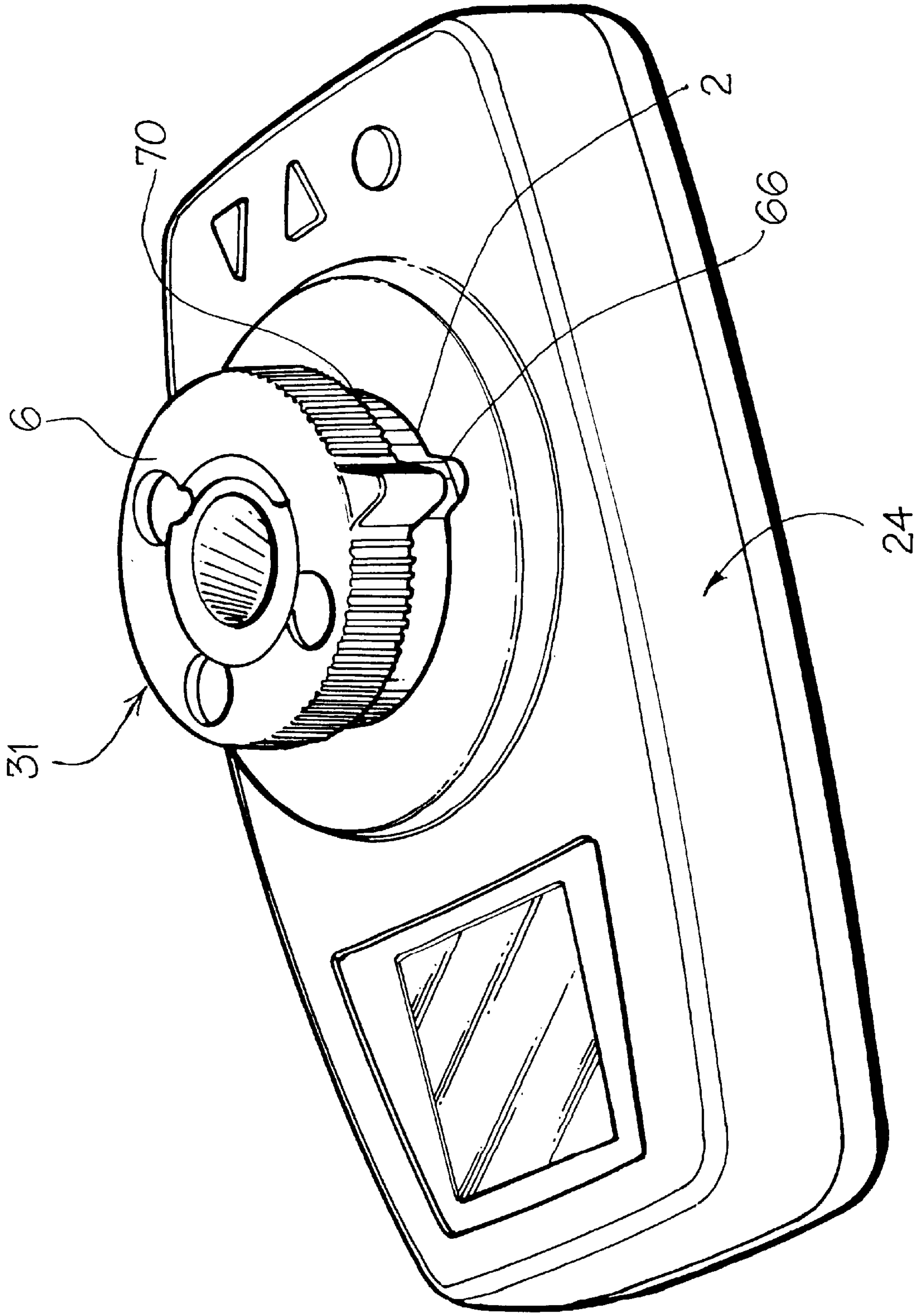
FIG. 9 is a perspective view of a preferred device comprising the apparatus as illustrated to FIGS. 5 and 6 and the instrument as illustrated in FIG. 8.

The most preferred apparatus and instrument are illustrated with reference to FIGS. 5, 6, and 8 and together they form a device as illustrated in FIG. 9.

Figure 5:
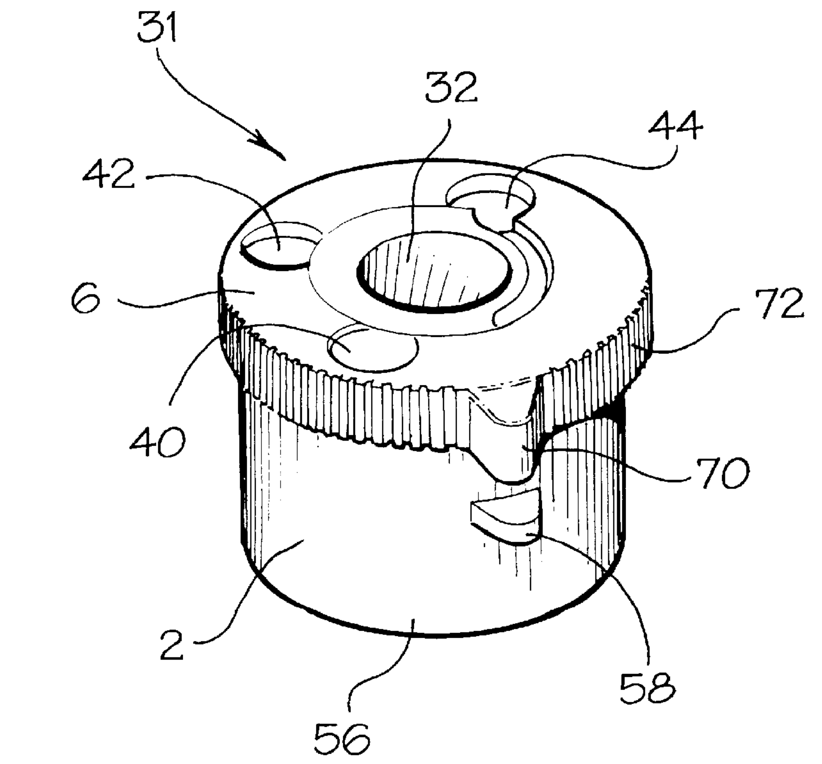
FIG. 5 is a perspective view of a preferred embodiment of an apparatus of the invention.
Figure 7:
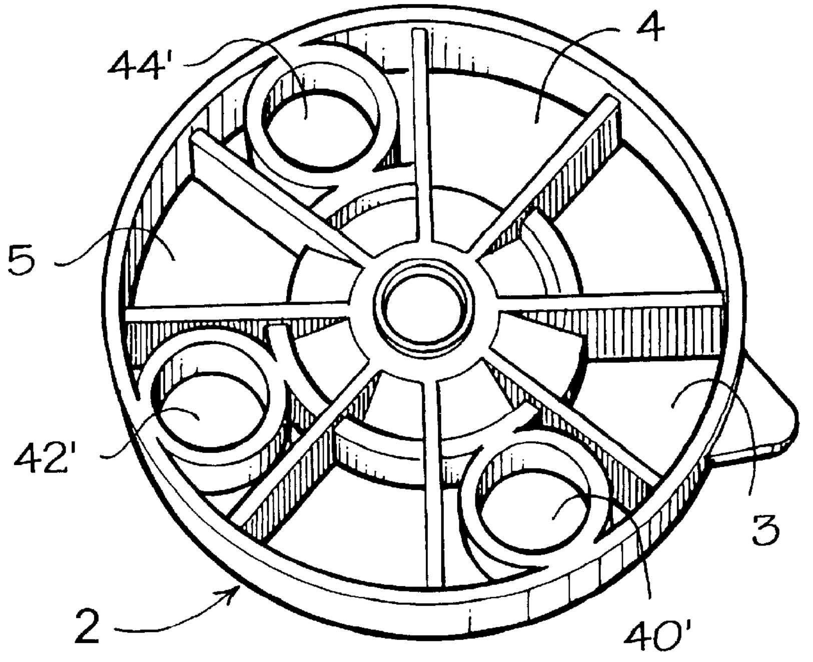
FIG. 7 is a perspective view of the base portion of the apparatus of FIGS. 5 and 6.
Figure 6:
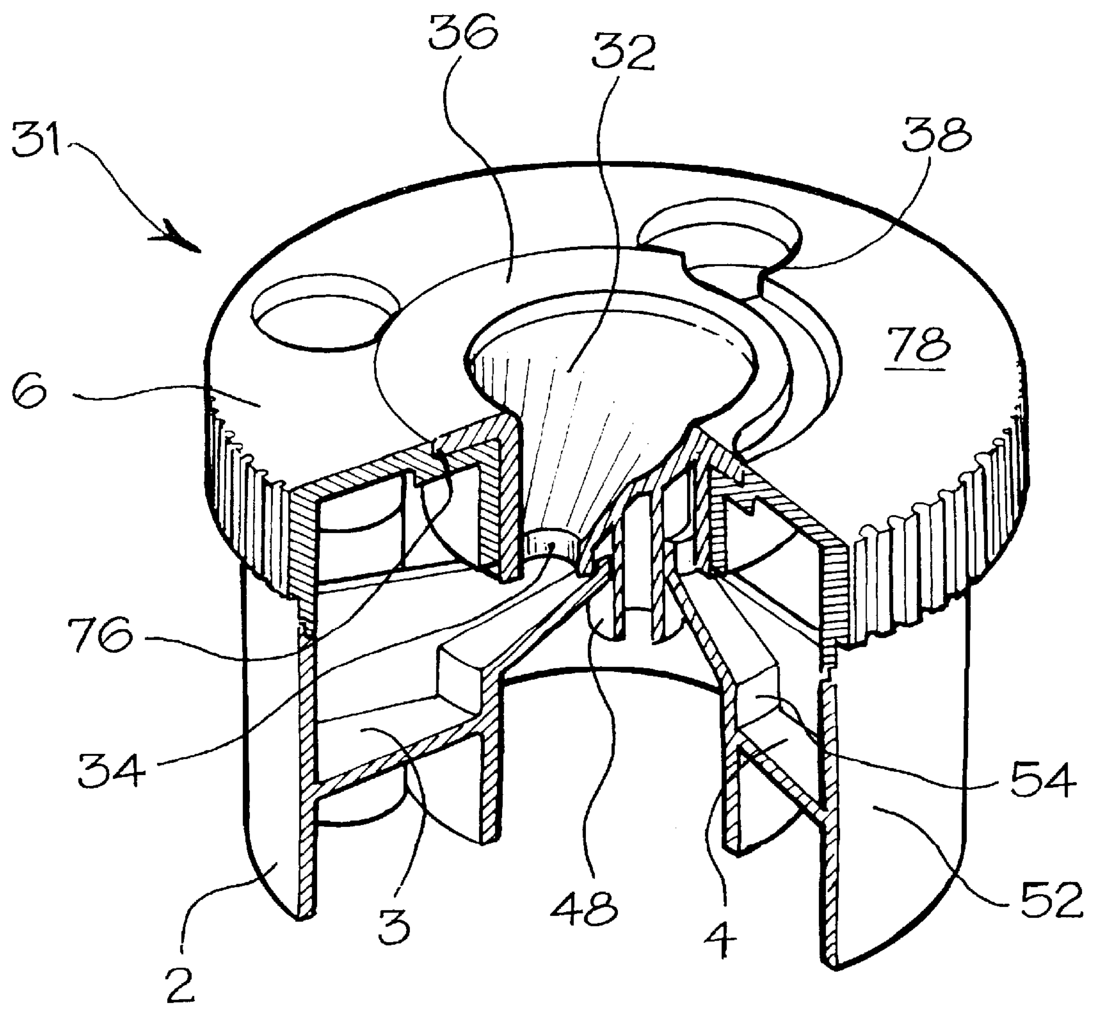
FIG. 6 is a partially sectioned view of the FIG. 5 apparatus.

Referring to FIGS. 5 and 6 the apparatus 31 comprises a base section 2 of clear plastics (shown in detail in FIG. 7), a top portion 6 and a funnel portion 32. The funnel portion 32 is made of a hydrophobic plastics and has a relatively large aperture to simplify emptying the reagents therein. It has an outlet 34 which directs the liquid into the optical chambers 3 and 5 when the apparatus is rotated in an instrument. The outlet 34 includes a frit (not shown) which frit serves to retain particles such as, for example, an amino phenyl boronate agarose affinity matrix. The funnel 32 which serves as an inlet port has an annular rim 36 with a recessed portion 38. The rim 36 partially overlies apertures 40, 42 and 44 formed in the top portion 6 of the apparatus such that tubes vertically disposed in the apparatus cannot pass through the respective apertures until the apertures are aligned with the recessed portion 38 of the annular rim. Projecting from the underside of the funnel is a stem 48 with a female mating member via which the apparatus 31 is connected to the instrument 24 which has a male member 50 adapted to engage it. The male member 50 holds the funnel in a fixed position relative to the instrument 24 such that the base portion 2 and top portion 6 of the apparatus 31 which together form a carousel rotate around the funnel, the annular rim 36 of the funnel serving as a guide means.

The base portion 6 of the apparatus is made of a clear plastics, is generally annular in shape and is divided into a plurality of compartments. As can be seen from FIG. 7 there are two optical chambers 3 and 5, a third chamber 4, for receiving waste from a wash step, which third chamber is disposed between optical chambers 3 and 5, and three additional chambers 40', 42' and 44' each housing a reagent tube. These chambers 40', 42' and 44', which are disposed below apertures 40, 42 and 44 in the top portion 6 of the apparatus 31, are arranged so that the reagent tubes are present to the user when the carousel is in the position corresponding to positions IV, VI and VII per FIG. 4*a* or position 1, 2 and 3 as per FIG. 4*b*. The optical chambers have a curved outer wall 52 and a curved inner wall 54 of optical quality, which help focus light from the LED's of the instrument 24 through the sample in the chamber to photodiodes at the other side thereof.

Each optical chamber 3, 5 can be brought into liquid communication with the outlet 34 of the funnel inlet port 9. Alternatively, the optical chambers can be recessed. Extending outwardly from the outermost wall 56 of the base portion 2 is a guide member 58 which sits within a circumferential channel member 60 formed on the outermost wall 62 of the annular recess 64 of the instrument 24. A communicating channel 66 which extends from the channel member 60 in outermost wall 62 of the top face 68 of the instrument 24 allows the guide member 58 to be inserted into the channel member 60 when the apparatus 31 is connected to the instrument 24.

A projecting member or tab 70 on the knurled edge 72 of the top portion 6 acts as an indicator means, denoting the position for locating the apparatus on the instrument and serves to assist in the turning of the apparatus.

The base portion 2 is connected to the top portion and the funnel portion sits in a channel 76 formed by a step on the top surface 78 of the top portion 6.

The instrument illustrated in FIG. 8 has been designed for use with an apparatus as herein before described. In essence it is very similar to the instrument described with reference to FIGS. 2, 3 and 4*b*. The instrument illustrated with reference to FIG. 8 does, however, differ from that described with reference to FIG. 2 in one major way and has a number of novel and advantageously beneficial additional features. Thus, in contrast to the instrument described with reference to FIG. 2 the lithium thionyl chloride battery and battery conditioning circuit is replaced with a power management and monitoring circuit so that the instrument can be connected to, for example, an external dc supply or a car battery. Additionally, the instrument is provided with communication system such as, for example, a RS232 thereby providing means for sending and receiving instructions and down loading data.

Significantly, the means for receiving the apparatus is an annular recess 64 in the instrument which is defined by a floor, an outermost sidewall 62 and an innermost sidewall 80.

In use the apparatus is inserted into the annular recess 64 by aligning guide member 58 of the apparatus with connecting channel 66 so that the apparatus is connected to male mating member 50 via its female mating member 48. The guide member 58 can thus enter channel member 60 such that it can be rotated. On rotation a first tube is directed up the ramp 82 and out of its aperture 44 since the recessed portion 38 of the annular ring 36 is aligned with the aperture. In this position the outlet 34 is in liquid communication with the first optical chamber 3 and the first step of the assay described with reference to FIGS. 4*a* and 4*b* can be conducted. By turning the apparatus through a further 90° a wash solution is presented through aperture 42 for use and then on turning the apparatus through a further 90° tube 40, the eluting solution, is presented. In this manner the appropriate reagents are presented for each step of the assay process.

The apparatus and instrument of the invention can be adapted for use in a number of assays.

In particular the instrument can be modified to read at wavelengths other than the 400 to 500 nm, more particularly 410 to 460 nm, range of the blue LED employed for measuring glycated haemoglobin. Thus, for example coloured light, red, green, yellow etc. LET's or white light and the use of optical fibres more preferably wavelength filters could be employed.

Also the apparatus could be modified to make single measurement rather than take several readings as exemplified with reference to the assay described where a percentage figure is calculated from two readings requiring a separation step. Thus, the inlet port and first and second inlets could be replaced by a carousel type apparatus carrying one or a plurality of optical chambers.

The type of assays might, for example, include:

1. ELISA type assays;
2. Affinity chromatography assays; and
3. Chemical analysis of analytes.

Thus, the wave length spread of the instrument could be adapted to measure the two most commonly used ELISA substrates ABTS which is measured at 414 nm and TMB which can be measured at 600 nm (blue) or 450 nm (yellow).

Affinity chromatography assays could be used to determine the presence and/or quantify a number of analytes using spectrophotometric analysis by selecting the appropriate wavelength.

Finally, the technology described could be utilised for field testing of chemical analytes. Thus, for example, water and soil analysis in which nitrates or sulphates are calculated or enzyme activity determined are envisaged.

The skilled man will appreciate that the device of the type described herein and its component apparatus and instrument could be used to measure levels of various other analytes in a wide range of samples.

What is claimed is:

1. An apparatus for use in an assay in which a sample is separated into component fractions for presentation to an instrument, said apparatus comprising:

a carousel, including, (1) a base portion having (a) a first inlet and a first component fraction collection chamber defined therein, said first inlet being in fluid communication with said first component fraction collection chamber, and (b) a second inlet and a second component fraction collection chamber defined by said base portion, said second inlet being in fluid communication with said second component fraction collection chamber, wherein said first and second component collection fraction chambers are not in fluid communication with each other, and (2) a top portion; and a funnel portion including an outlet port, said funnel portion being adapted to receive a filter means or a binder means, wherein said carousel is rotatably mounted about said funnel portion such that when said carousel is rotated, said outlet port is brought into selective liquid communication with each first and second inlet in turn.

2. An apparatus in accordance with claim 1 wherein the filter means or binder retaining means is a frit.

3. An apparatus in accordance with claim 1 wherein said first and second inlets include optical chambers.

4. An apparatus in accordance with claim 1 further comprising a third inlet.

5. An apparatus in accordance with claim 4 further comprising an absorbent or wicking material positioned in said third inlet.

6. An apparatus in accordance with claim 1 wherein the funnel portion further comprises:

means for locating the funnel portion relative to an optical instrument.

7. An apparatus in accordance with claim 1 wherein the funnel portion further comprises:

a guide member about which the carousel rotates.

8. An apparatus in accordance with claim 7 wherein the guide member includes an annular ring.

9. An apparatus in accordance with claim 8 wherein the annular ring includes a recessed portion.

10. An apparatus in accordance with claim 1, wherein the carousel is adapted to house a plurality of tubes and the top portion includes a plurality of holes formed therein adapted for removal of said tubes from the apparatus.

11. An apparatus in accordance with claim 1 wherein the first and second inlets are optical chambers.

12. An apparatus in accordance with claim 11 wherein the optical chambers have curved optical surfaces.

13. An apparatus in accordance with claim 12 wherein the optical chambers are recessed.

14. An apparatus in accordance with claim 1, further comprising:

an instrument adapted for receiving the carousel, comprising:

a microprocessor operable via a key pad, at least one light emitter;

at least one light detector;

a display and driver;

an analog to digital converter; and means for connecting the instrument to a power source.

15. An apparatus in accordance with claim 14, further comprising an annularly shaped recessed portion in said instrument for receiving said carousel, said recessed portion defined by a floor, an annular innermost side wall extending from said floor and an annular outermost sidewall extending from said floor, said outermost side wall comprising a channel member running about its circumference and a connecting channel extending from a top surface of the instrument to the channel member.

16. A method for assaying a sample with an apparatus having (A) a carousel which includes (1) a base portion having (a) a first inlet and a first component fraction collection chamber defined therein, said first inlet being in fluid communication with said first component fraction collection chamber, and (b) a second inlet and a second component fraction collection chamber defined by said base portion, said second inlet being in fluid communication with said second component fraction collection chamber, and (2) a top portion having (B) a funnel portion including an outlet port adapted to receive a filter means or a binder means, said carousel being rotatably mounted about said funnel portion such that as said carousel is rotated, said outlet port is moveable relative to each of said first and second inlets and is brought into selective liquid communication with each first and second inlet in turn, said method comprising the steps of:

collecting a first component fraction of the sample into the first component fraction collection chamber, rotating said carousel about said funnel portion;

collecting a second component fraction of the sample into the second component fraction collection chamber; and assaying the first and second component fractions to determine the presence or absence of one or more analytes in said component fractions.

17. A method of assaying in accordance with claim 16, wherein the sample is blood, the first component fraction contains one or more non-glycated proteins, and the second component fraction contains one or more glycated proteins.

18. A method of assaying in accordance with claim 17, wherein the one or more glycated proteins are selected from the group consisting of glycated hemoglobin, glycated human serum albumin and glycated apo lipoprotein.

19. A method of assaying in accordance with claim 18 further comprising the following steps of:

obtaining a blood sample containing blood cells from a subject;

lysing blood cells of the blood sample; and separating the blood sample into two components using a method which involves binding an analyte to a solid phase to obtain a first component fraction and then releasing the analyte to obtain the second fraction.

20. A method of assaying in accordance with claim 19, further comprising the steps of:

separating the analyte from the sample; and detecting the analyte by immunoassay or spectrophotometry.

* * * * *